United States Patent
Siejko et al.

(10) Patent No.: US 10,646,131 B2
(45) Date of Patent: May 12, 2020

(54) BRADY PAUSE DETECTION FOR IMPLANTABLE CARDIAC MONITORS

(71) Applicant: Cardiac Pacemakers, Inc., St. Paul, MN (US)

(72) Inventors: Krzysztof Z. Siejko, Maple Grove, MN (US); Derek D. Bohn, Woodbury, MN (US); David L. Perschbacher, Coon Rapids, MN (US); Adam MacEwen, White Bear Lake, MN (US); Sunipa Saha, Shoreview, MN (US); Keith L. Herrmann, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 223 days.

(21) Appl. No.: 15/697,756

(22) Filed: Sep. 7, 2017

(65) Prior Publication Data

US 2018/0064360 A1 Mar. 8, 2018

Related U.S. Application Data (60) Provisional application No. 62/384,408, filed on Sep. 7, 2016.

(51) Int. Cl.
*A61B 5/04* (2006.01)
*A61B 5/0452* (2006.01)
(Continued)

(52) U.S. Cl.
CPC .......... *A61B 5/0452* (2013.01); *A61B 5/0006* (2013.01); *A61B 5/04014* (2013.01);
(Continued)

(58) Field of Classification Search
USPC ........................................................ 600/513
See application file for complete search history.

(56) References Cited

U.S. PATENT DOCUMENTS

2007/0038253 A1\* 2/2007 Kim ................... A61B 5/04011
607/4
2008/0275516 A1 11/2008 Ghanem et al.
(Continued)

FOREIGN PATENT DOCUMENTS

| CN | 109688916 A | 4/2019 |
| JP | 2019529014 A | 10/2019 |
| WO | WO-2018048992 A1 | 3/2018 |

OTHER PUBLICATIONS

Krahn, Andrew, "R-Wave Sensing in an Implantable Cardiac Monitor without ECG-Based Preimplant Mapping: Results from a Multicenter Clinical Trial", PACE, vol. 37, (Apr. 2014), 505-511.
(Continued)

*Primary Examiner* — Christopher Koharski
(74) *Attorney, Agent, or Firm* — Schwegman Lundberg & Woessner, P.A.

(57) ABSTRACT

An apparatus includes a cardiac signal sensing circuit configured to generate a sensed cardiac signal representative of electrical cardiac activity of a subject, a buffer memory and a pause detection circuit. The pause detection circuit is configured to: identify ventricular depolarization in the cardiac signal or the sampled cardiac signal; detect a candidate pause episode using the cardiac signal in which delay in ventricular depolarization exceeds a specified delay threshold; identify noise events in a stored cardiac signal; and discard the cardiac signal of the candidate pause episode when a number of noise events satisfies a specified noise event number threshold, otherwise store the cardiac signal of the candidate pause episode as a bradycardia pause episode.

20 Claims, 7 Drawing Sheets

(51) Int. Cl.
  *A61B 5/00*      (2006.01)
  *A61B 5/0468*    (2006.01)
  *A61B 5/0456*    (2006.01)
  *A61B 5/0464*    (2006.01)
  *G06F 19/00*     (2018.01)
  *A61N 1/39*      (2006.01)
  *A61N 1/37*      (2006.01)

(52) U.S. Cl.
  CPC .......... *A61B 5/0456* (2013.01); *A61B 5/0464* (2013.01); *A61B 5/0468* (2013.01); *A61B 5/7207* (2013.01); *A61B 5/7214* (2013.01); *A61B 5/0031* (2013.01); *A61B 5/04012* (2013.01); *A61N 1/37* (2013.01); *A61N 1/3925* (2013.01); *G06F 19/3418* (2013.01)

(56) References Cited

U.S. PATENT DOCUMENTS

| | | |
|---|---|---|
| 2009/0018595 A1 | 1/2009 | Bharmi et al. |
| 2012/0203123 A1 | 8/2012 | Mahajan et al. |
| 2016/0000350 A1 | 1/2016 | Zhang |

OTHER PUBLICATIONS

Sarkar, Shantanu, et al., "A dual sensing scheme to reduce inappropriate detection of bradycardia and pauses in an insertablecardiac monitor", Heart Rhythm Society (HRS) Conference, May 4, 2016, 15 pgs.

"Australian Application Serial No. 2017325013, First Examination Report dated Jun. 24, 2019", 3 pgs.

"Australian Application Serial No. 2017325013, Response filed Sep. 26, 2019 to First Examination Report dated Jun. 24, 2019", 17 pgs.

"Australian Application Serial No. 2017325013, Subsequent Examiners Report dated Oct. 28, 2019", 3 pgs.

"European Application Serial No. 177772161.0, Response to Communication Pursuant to Rules 161 & 162 filed Oct. 10, 2019", 15 pgs.

"International Application Serial No. PCT/US2017/050414, International Preliminary Report on Patentability dated Mar. 21, 2019", 8 pgs.

"International Application Serial No. PCT/US2017/050414, International Search Report dated Nov. 30, 2017", 5 pgs.

"International Application Serial No. PCT/US2017/050414, Written Opinion dated Nov. 30, 2017", 8 pgs.

\* cited by examiner

BRADY PAUSE DETECTION FOR IMPLANTABLE CARDIAC MONITORS

CLAIM OF PRIORITY

This application claims the benefit of priority under 35 U.S.C. § 119(e) of U.S. Provisional Patent Application Ser. No. 62/384,408, filed on Sep. 7, 2016, which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs), insertable cardiac monitors (ICMs) and subcutaneously implantable heart monitors (SubQ HMs). The devices may include electrodes in communication with one or more sense amplifiers to monitor electrical heart activity within a patient, or can include one or more sensors to monitor one or more other internal patient parameters. Subcutaneously implantable devices may include electrodes that are able to sense cardiac signals without being in direct contact with the patient's heart. Other examples of implantable devices include implantable drug delivery systems or implantable devices with neural stimulation capability (e.g., vagus nerve stimulator, baroreflex stimulator, carotid sinus stimulator, spinal cord stimulator, deep brain stimulator, etc.).

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include personal data assistants (PDAs) and smartphones. The handheld devices can be diagnostic devices that record an electrocardiograph (ECG) or other physiological parameter while the device is resting in the patient's hand or being held to the patient's chest. The devices may derive measurements associated with a cardiac depolarization of the patient. The measurements can provide useful information concerning the health of the patient. Knowledge regarding the physiological condition of the patient can be useful to physicians and clinicians for diagnostic purposes or to tailor performance of a medical device to that patient's needs to provide the most effective patient therapy.

OVERVIEW

It can be desirable for ambulatory medical devices to correctly detect and identify cardiac arrhythmias. Detection of bradycardia pause can help physicians and clinicians assess the condition of the patient and may help in customizing a prescribed bradycardia treatment device to the patient's needs.

One example apparatus of the present subject matter can include a cardiac signal sensing circuit configured to generate a sensed cardiac signal representative of electrical cardiac activity of a subject; a buffer memory configured to store at least a portion of the cardiac signal; and a pause detection circuit electrically coupled to the cardiac signal sensing circuit and the buffer memory. The pause detection circuit is configured to identify ventricular depolarization in the cardiac signal or the sampled cardiac signal; detect a candidate pause episode using the cardiac signal in which delay in ventricular depolarization exceeds a specified delay threshold; identify noise events in a stored cardiac signal; and discard the cardiac signal of the candidate pause episode when a number of noise events satisfies a specified noise event number threshold, otherwise store the cardiac signal of the candidate pause episode as a bradycardia pause episode.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

Figure 1:
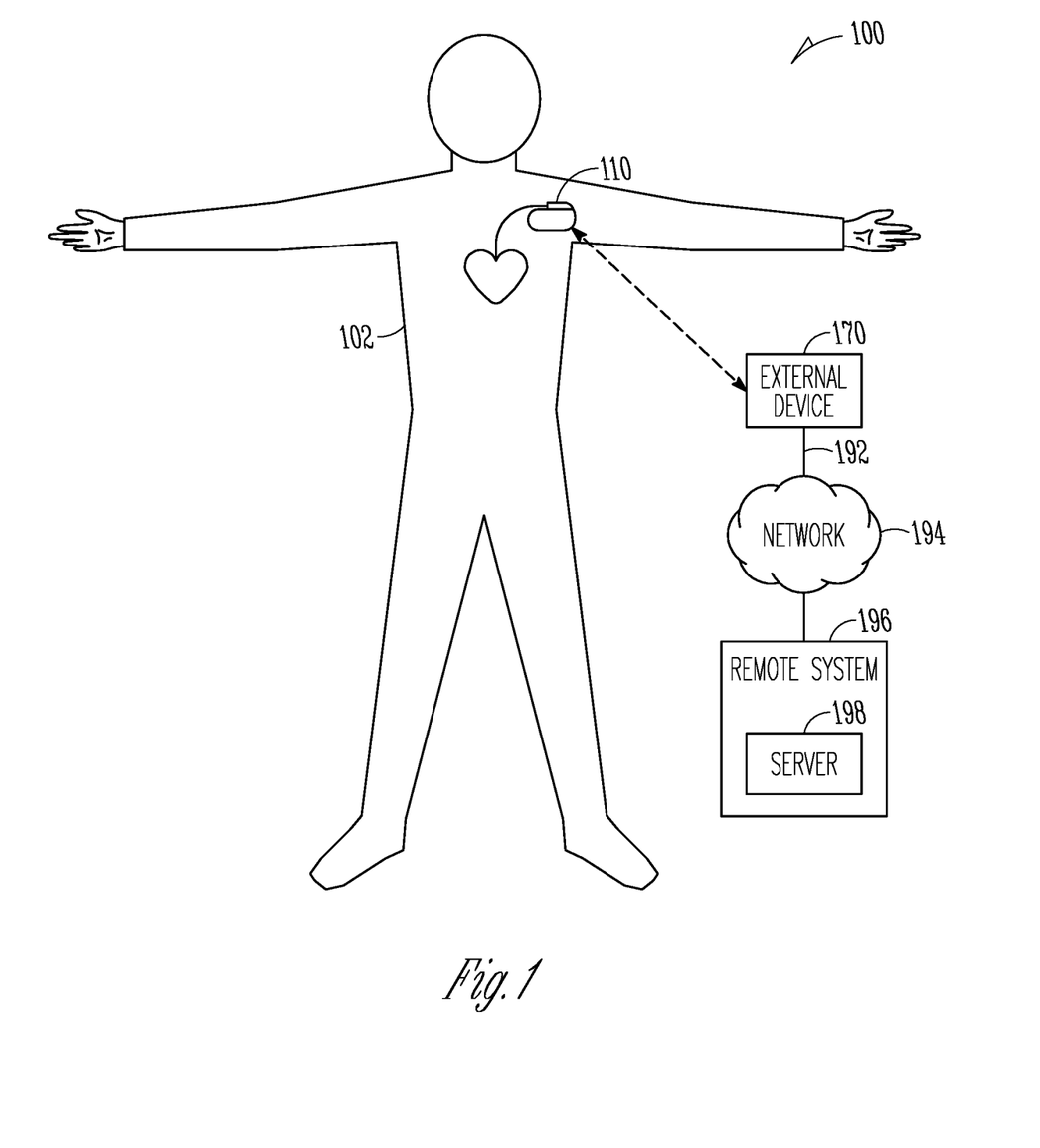
FIG. 1 is an illustration of portions of an example of a system that uses an ambulatory medical device to provide a therapy to a patient.

FIG. 1 is an illustration of portions of an example of a system 100 that uses an implantable medical device 110 to provide a therapy to a patient 102. The system 100 typically includes an external device 170 that communicates with a remote system 196 via a network 194. The network 194 can be a communication network such as a cellular telephone network or a computer network (e.g., the internet). In some examples, the external device includes a repeater and communicated via the network using a link 192 that may be wired or wireless. In some examples, the remote system 196 provides patient management functions and may include one or more servers 198 to perform the functions.

Ambulatory medical devices can provide device-recorded information related to cardiac function of the patient or subject. For example, an IMD can include one or more sense amplifier circuits to produce sensed signals representative of cardiac depolarization of the patient. The sensed signals can be sampled and stored in the device as electrograms for later uploading and analysis. Optimizing the recording of the information can lead to more accurate information being collected by a device, which can lead to improved treatment of the patient's condition (e.g., for bradycardia) and more effective device-based therapy provided to the patient.

A bradycardia pause, or brady pause, is an episode in which the interval between cardiac contractions exceeds a specified duration (e.g., because of a very slow beat or a skipped beat). Brady pause detection can be a desirable feature for ambulatory ECG monitoring devices. Frequent pauses may explain occurrence of syncope for the patient and may indicate when a pacemaker needs to be prescribed for the patient to address atrial-ventricular (AV) block or sick sinus syndrome.

An ICM or ILR can be an effective tool for diagnosing and monitoring patients. The size of the device, ease of implant procedure, ability to record electrocardiographs (ECGs), and battery longevity enable longer-term monitoring of patients that may otherwise not be possible with external patches or Holter recorders. The short distance between sensing electrodes can provide high quality sensing and R-wave detection for interval-based arrhythmia detection and other monitoring purposes.

However, the rate at which conventional ILRs and ICMs detect false brady pauses can be high. Recorded false brady pauses can lead to unnecessary time spent in clinician review of the device recordings. Detection of false brady pauses can be caused by under-sensing of R-waves. An R-wave refers to a deflection in an ECG signal that is representative of a portion of ventricular depolarization. R-waves with very low amplitude may be missed by the sense amplifiers of the monitoring device. Also, monitoring devices may include automatic gain control (AGC) or dynamic threshold sensing in heartbeat detection that can complicate brady pause detection.

For dynamic thresholds, the detection threshold amplitude tracks the detected R-wave amplitude. The detection threshold is set higher for higher amplitude R-waves. If no R-wave meets the detection threshold, the threshold value decays to a minimum value or until the next R-wave is detected. Setting the correct dynamic threshold for brady pause detection can be complicated by events that can cause a temporary change in amplitude of R-waves. For instance, a shift in posture of the patient may temporarily reduce the amplitude of R-waves. Other events may cause a temporary increase in R-wave amplitude, such as signal noise due to skeletal muscle movement. The temporary change in R-wave amplitude may cause a device to miss detection of R-waves due to latency of adjustment in the dynamic threshold detection.

Figure 2A:
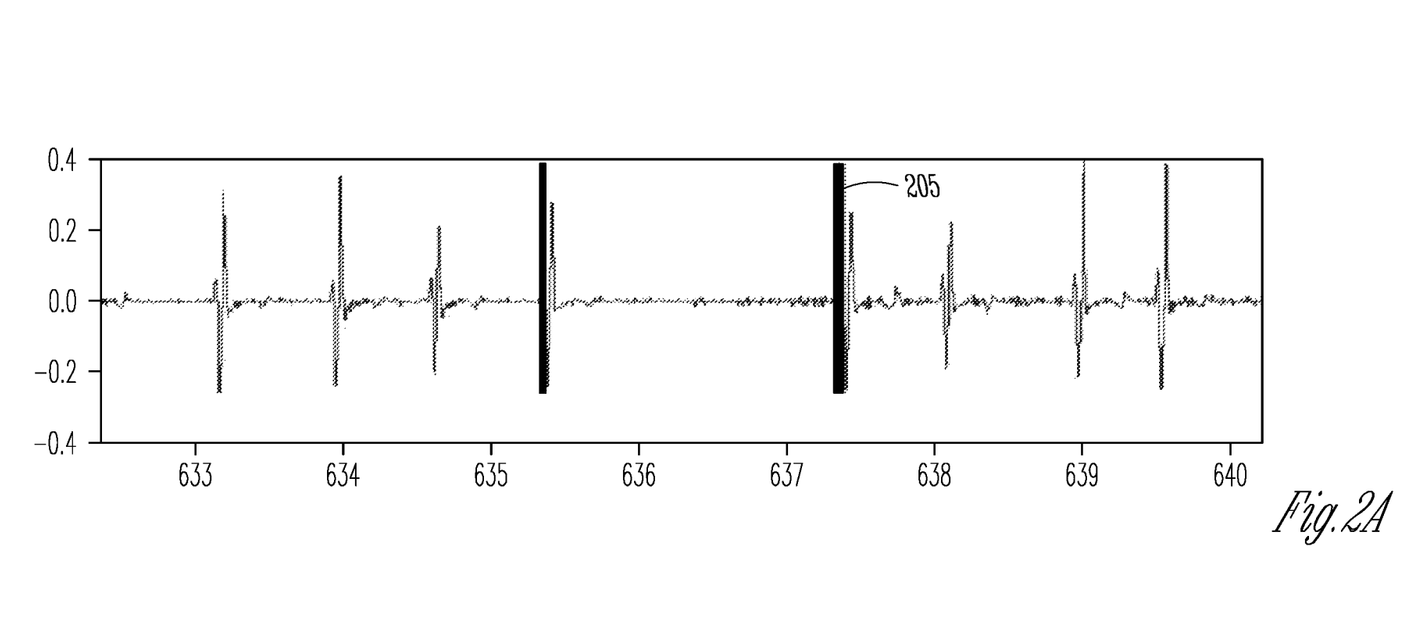
FIGS. 2A and 2B are graphs of signal waveforms representative of ventricular depolarization.
Figure 2B:
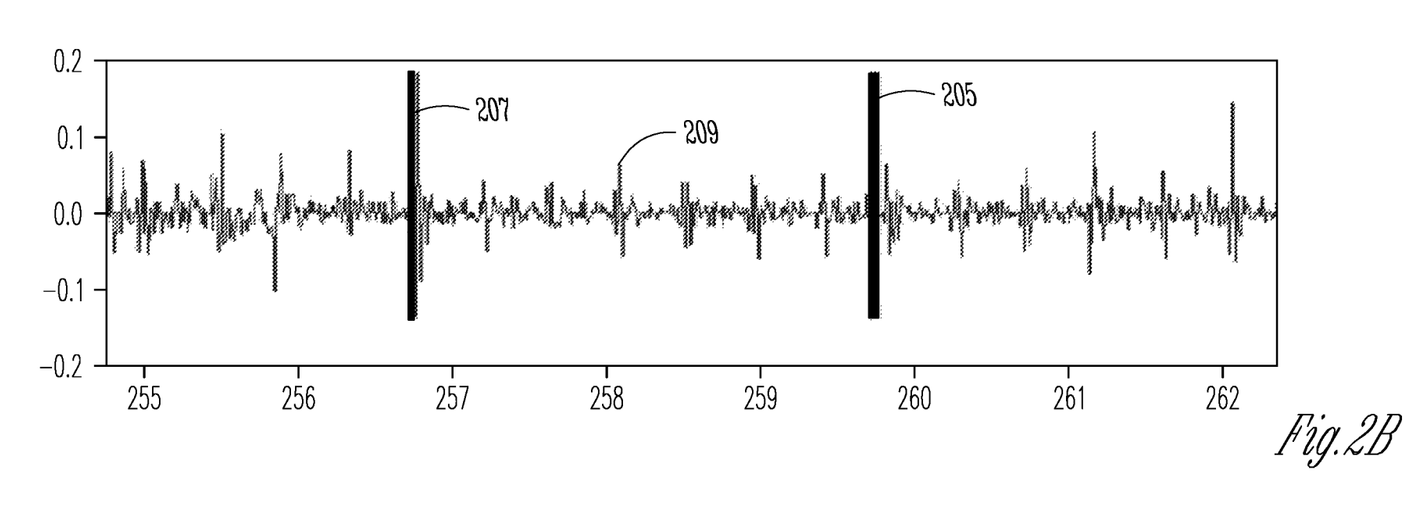

FIGS. 2A and 2B are graphs of signal waveforms representative of ventricular depolarization. FIG. 2A shows a true episode of brady pause. The threshold for the time duration between R-waves for detection of brady pause is set to two seconds. The graph includes a pause marker 205 to indicate the brady pause. The signal waveform is essentially a flat line between the last R-wave before the pause and the marker. FIG. 2B shows a false brady pause. In this example, the threshold for the duration between R-waves for detection of brady pause is set to three seconds. The pause marker 205 indicates when brady pause was incorrectly declared. The large R-wave 207 before the pause marker raised the dynamic detection threshold. The subsequent R-waves of smaller amplitude 209 are missed due to the latency in the adjustment of the dynamic threshold causing the detection of a false brady pause.

Figure 3:
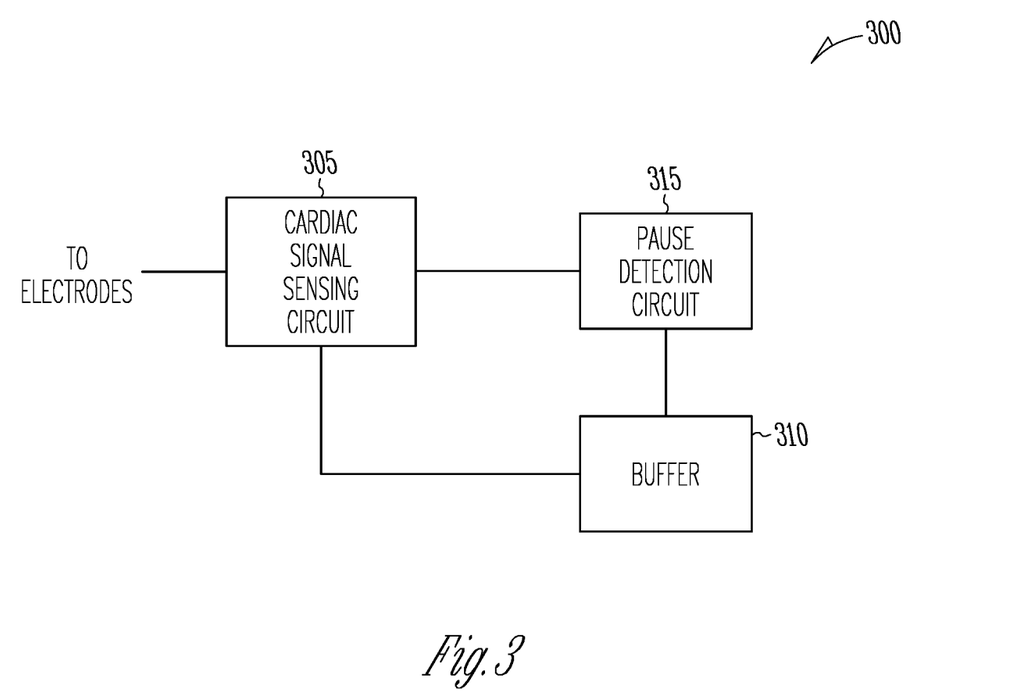
FIG. 3 is a block diagram of portions of an example of an ambulatory medical device.

FIG. 3 is a block diagram of portions of an example of an ambulatory medical device. The device 300 includes a cardiac signal sensing circuit 305 that may be operatively coupled to electrodes, a buffer memory 310, and a pause detection circuit 315. The cardiac signal sensing circuit 305 generates a sensed cardiac signal representative of electrical cardiac activity of a subject. The buffer memory 310 stores at least a portion of the sensed cardiac signal. The pause detection circuit 315 may include one or more of a microprocessor, a digital signal processor, application specific integrated circuit (ASIC), or other type of processor, interpreting or executing instructions included in software or firmware. The pause detection circuit 315 identifies ventricular depolarization in at least one of the sensed cardiac signal. In certain examples, the pause detection circuit 315 identifies ventricular depolarization by detecting R-waves the cardiac signal. The pause detection circuit 315 detects candidate pause episodes using sensed cardiac signals. The candidate pause episodes are identified when delay in depolarization of the ventricles exceeds a specified (e.g., programmed) time delay threshold.

The pause detection circuit 315 processes the cardiac signals of candidate pause episodes to identify noise events in the sensed cardiac signal and discards the sensed candidate pause signal of the candidate pause episode when a number of noise events satisfies a specified noise event number threshold. Otherwise, the sensed cardiac signal for the candidate pause episode is stored as a brady pause episode. In some examples, storing the sensed cardiac signal as a true brady pause episode includes flagging the area of memory as a brady pause episode, and discarding the sensed cardiac signal includes not flagging the area of memory and allowing the area of memory to be overwritten.

In some examples, the buffer memory 310 includes a temporary buffer that stores segments of one or more cardiac signals as they are sensed and sampled. The temporary buffer may be a circular buffer in which data is overwritten when the buffer is filled. If the episode is determined to be a true brady pause episode, the cardiac signal segment that includes the brady pause may be transferred to a different more permanent area of memory for later uploading. If the candidate pause episode is to be discarded, it may be left in the temporary buffer to eventually be overwritten.

The brady pause detection can be viewed as a two-tiered approach. In the first tier, the candidate pause episodes are determined based on intervals between depolarization (e.g., R-R intervals). If a sensed depolarization interval exceeds a specified threshold time interval (e.g., 3 seconds), the interval is identified as a candidate pause episode. The candidate pause episode is then further processed in the second tier to determine whether the candidate pause episode is a true brady pause episode.

Figure 4:
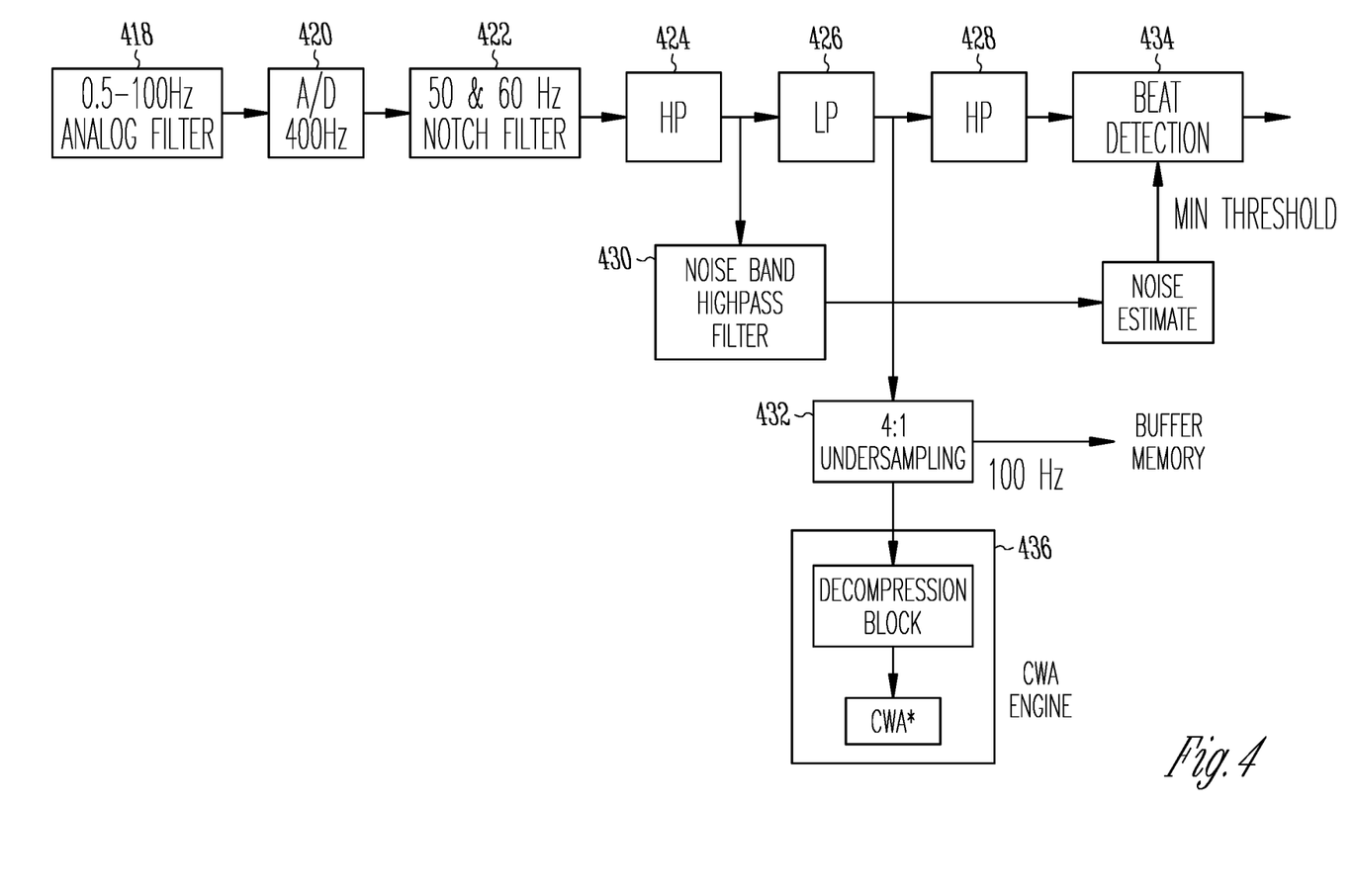
FIG. 4 is a block diagram of an example of cardiac signal sensing circuitry for detection of cardiac depolarization.

FIG. 4 is a block diagram of an example of cardiac signal sensing circuitry for detection of cardiac depolarization. The circuitry includes an analog filter 418, analog to digital converter (A/D) 420, and notch filters 422. The analog filter 418 may be a bandpass filter with pole frequencies of 0.5 Hertz (0.5 Hz) and 100 Hz to produce a filtered baseline signal. The notch filters may have notch frequencies of 50 Hz and 60 Hz. The notch filtering is useful to remove electromagnetic interference (EMI). In some examples, the A/D 420 has a sample rate of 400 Hz, and the notch filters are implemented using one or more digital signal processors (DSPs).

The next stage of the signal processing includes a series of high pass and low pass filtering. Sensed signals may be processed differently for noise detection and depolarization detection. In the example of FIG. 4, the sensed signal is applied to a first high pass filter 424 to create a wideband signal. In some examples the pole frequency of the first high pass filter is 3 Hz and the high pass filtering attenuates wander in the baseline signal. Baseline wander can result from patient motion or myopotential noise. The 3 Hz high pass may also reduce or remove very low frequency signal components (e.g., due to respiration) that are not of interest in detecting brady pause. At this point the signal processing diverges to process signals for depolarization detection and noise analysis.

For depolarization detection, the signal is applied to a low pass filter 426. If depolarization is to be detected using R-waves, the pole frequency of the low pass filter can be 40 Hz. The relative energy of spectral components above 40 Hz in the QRS complex can be small. The signal after this stage can be down-sampled at 432 (nominally to 100 Hz), amplitude-compressed to 8 bits, and stored in the buffer memory. This is also the signal stored for a candidate pause episode. This representation of the signal is sufficient to distinguish the relevant ECG features, such as morphology analysis for example. The buffered signal produced by this stage may also be used in waveform morphology analysis (e.g., correlation waveform analysis (CWA) using CWA engine 436) because the morphology of the QRS complex is preserved. The buffer memory may be accessible by the firmware for any non-real-time processing.

The signal from the 40 Hz low pass can be applied to a second high pass filter 428. The pole frequency of the high pass filter may be 10 Hz to attenuate lower frequency ECG components such as P-waves and T-waves. P-waves are associated with atrial depolarization and precede the QRS complex in an electrocardiogram. T-waves follow the S-T segment of an electrocardiogram. The result of the filtering is a signal processed with a pass band from 10 Hz to 40 Hz that can be processed for R-wave detection. R-wave detection may include a dynamic detection threshold that is updated or adjusted on each cardiac cycle. The detection threshold tracks the detected R-wave amplitude based on specified parameters of the hardware circuits, and decays to a minimum value or until the next R-wave is detected.

For noise analysis, the signal from the first high pass filter is applied to a third high pass filter 430 which is a noise band high pass filter. In certain examples, the signal after the notch filters 422 is applied to the third high pass filter. Together with the result from the analog filter 418, the cardiac signal may be filtered to a band between 55 Hz and 100 Hz. This filtering is intended to pass a portion of the myopotential noise spectrum with minimal interference from signal energy included in an electrogram or electrocardiogram. One or more of the low pass filter 426 or high pass filters 424, 428, and 430 can be implemented with one or more digital signal processors.

The result of the signal processing by cardiac signal sensing circuitry is a wideband signal filtered to a specified frequency band (e.g., 3 Hz-100 Hz), and the wideband signal is split into two other frequency bands or ranges. A higher frequency band (e.g., 55 Hz-100 Hz) is used for noise analysis and a lower frequency band (e.g., 10 Hz-40 Hz) is used for cardiac depolarization detection and candidate pause episode identification. Additionally, a compressed signal is generated using the filtering (e.g., a passband of 3 Hz-40 Hz), stored and available for processing using the second tier of the brady pause episode detection.

Figure 5:
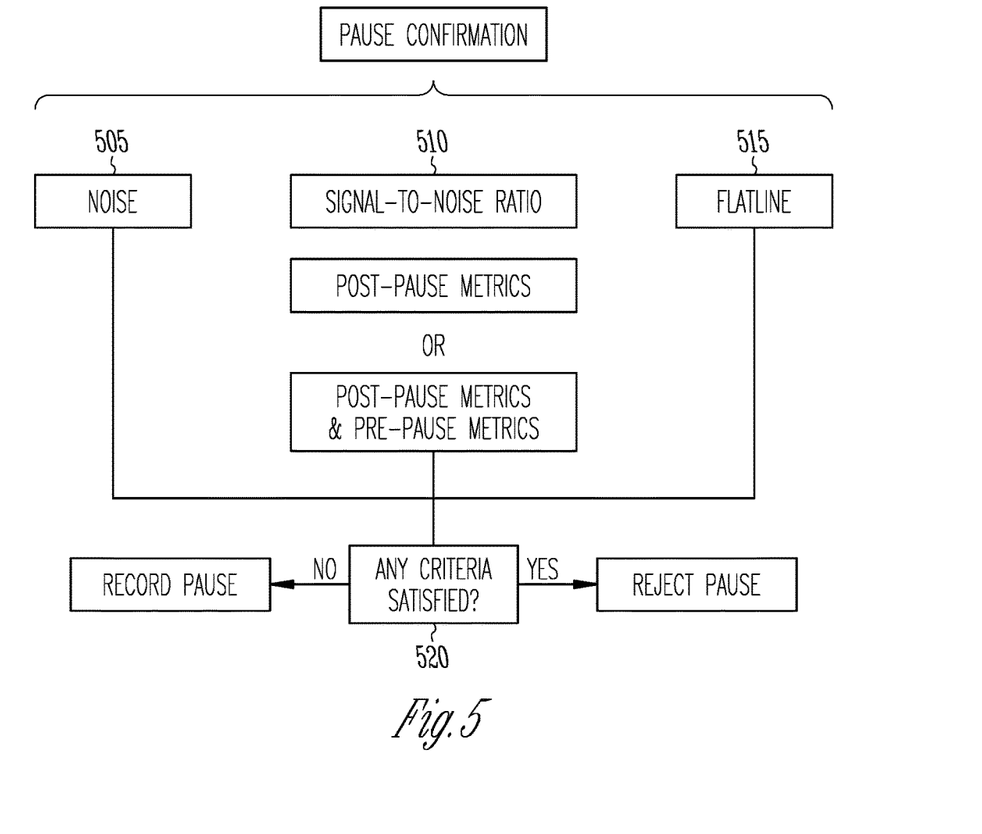
FIG. 5 is a flow diagram of a process of further evaluating a detected candidate pause episode to confirm bradycardia pause.

FIG. 5 is a flow diagram of a process of further evaluating a detected candidate pause episode to confirm brady pause. The evaluation uses three methods. At 505, noise on the sensed cardiac signal is characterized. At 510, one or more signal-to-noise metrics are determined for the stored signal to detect under-sensing. At 515, signals that include a flatline segment or have missing data are identified. At 520, if any of the methods meet the criteria for a false brady pause, the episode is rejected (e.g., discarded or not recorded).

The noise characterization method rejects candidate pause episodes that are deemed to be too noisy. Signal noise can be characterized using the higher frequency band signal produced from the wideband signal. The cardiac signal is mainly composed of signal energies less than 40 Hz. Using a high pass filter with a 55 Hz frequency pole removes the P-QRS-T complexes and any signal components above 55 Hz remain. Presence of a higher frequency signal in the higher band may indicate higher frequency narrow band noise that may subsequently raise the noise and cause R-wave under-sensing. A noise event may be a signal amplitude on the higher frequency band signal that exceeds a specified noise threshold amplitude value. The criteria for a false brady pause may include the number of detected noise events satisfying a specified noise event number threshold. The candidate pause episode can be stored as a brady episode when the number of detected noise events is less than the threshold.

For the signal-to-noise method, signal-to-noise metrics are used to determine if there is too much signal content during the candidate pause episode and to determine the likelihood that under-sensing of cardiac depolarization has occurred. The candidate pause episode may be stored or discarded according to one or more of the calculated signal metrics. The signal-to-noise metrics can include one or both of pre-pause signal-to-noise metrics and post-pause signal-to-noise metrics.

In some examples, the signal stored for a candidate pause episode in the buffer memory can be used to determine the signal-to-noise metrics. The pause detection circuit 315 of FIG. 3 may filter the stored signal before the measurements of the signal are made. If the stored signal was amplitude-compressed, the stored signal may amplitude-decompressed before filtering. High-pass filtering may then be applied to the amplitude-restored signal. In some examples a difference of consecutive samples is used for the high-pass filtering. The filtered value $y(n)$ of EGM sample $x(n)$ is the difference between consecutive decompressed samples: $y(n)=x(n)-x(n-1)$, where n is a sample number. This is similar to taking the first derivative. This high pass filtered signal may be used to measure R-wave amplitudes used in the signal-to-noise metrics. The high pass filtering is used to reproduce the 10-40 Hz beat detection band signal. An advantage of using this band is that it attenuates p-waves, which is useful for detecting pauses due to atrial-ventricular (AV) block. A prominent P-wave may cause a true pause to be rejected or missed by the pre-pause or post-pause signal-to-noise metrics.

Figure 6:
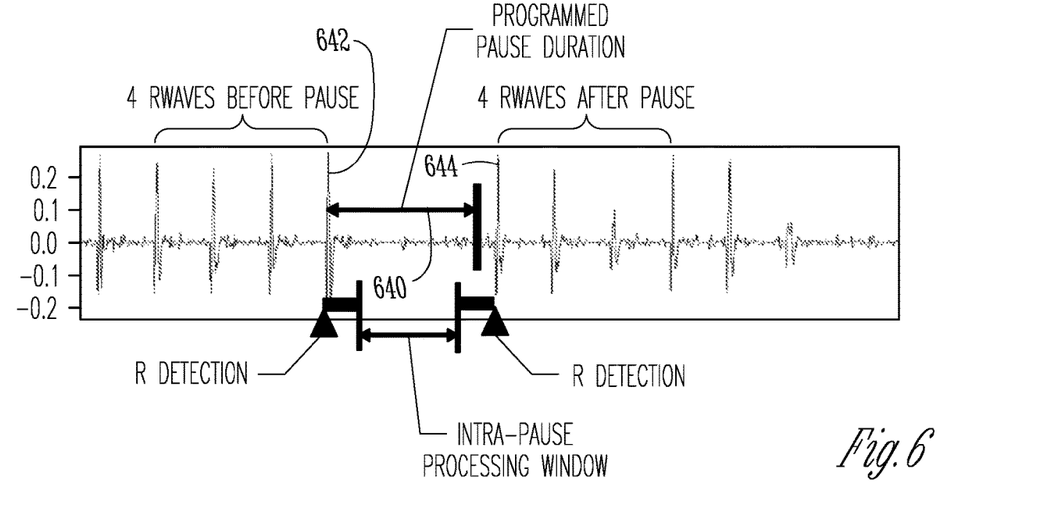
FIG. 6 is an illustration of signal processing used in calculating the signal-to-noise metrics of the signal for the candidate pause episode.

FIG. 6 is an illustration of signal processing used in calculating the signal-to-noise metrics of the signal for the candidate pause episode. The brady pause is evident in the candidate pause signal by the gap in R-waves. An intra-pause duration 640 is timed in the candidate pause signal. The timing of the intra-pause duration begins a specified time after the last R-wave sensed 642 before the detected candidate pause episode. In some examples, the intra-pause duration begins after a refractory period is timed for the last R-wave sensed 642. A refractory period refers to the period of time that sense amplifiers of a CFM are blanked or disabled to be unresponsive to intrinsic signal of the heart. The pause refractory may be a programmable pause refractory specifically used for brady pause detection.

The pause detection circuit may determine a pre-pause central tendency value (e.g., an average value or a mean value) of the amplitude of a specified number of R-waves identified prior to the candidate pause episode. In the example of FIG. 6, four R-waves are used in determining the pre-pause central tendency value.

The pause detection circuit may also calculate an intra-pause threshold of amplitude of signal samples during the intra-pause duration. These signal samples would be included after the last R-wave sensed 642 and before the first R-wave 644 sensed after the detected candidate pause. In some examples, the intra-pause threshold is calculated according to the amplitude of a specified fraction of the signal samples during the intra-pause duration. For instance, the intra-pause threshold may be calculated as a percentile amplitude value (e.g., the $95^{th}$, the $98^{th}$ percentile value, or even the $100^{th}$ percentile value) of the signal samples in the intra-pause duration window.

A criterion for determining a false brady pause may include the pre-pause central tendency value and the intra-pause threshold in a signal-to-noise metric. For instance, the pause detection circuit may calculate a ratio that includes the pre-pause central tendency value and the intra-pause threshold. The pause detection circuit discards the candidate pause episode or stores the candidate pause episode as a brady-cardia pause episode according to the pre-pause central tendency value and the intra-pause threshold. For instance, the pause detection may discard the candidate pause episode when a calculated ratio of the pre-pause central tendency value to the intra-pause threshold is less than a specified ratio threshold value.

The pause detection circuit may determine a post-pause central tendency value (or look-ahead central tendency value) of the amplitude of a specified number of R-waves identified after the candidate pause episode. In the example shown in FIG. 6, four R-waves are used in determining the post-pause central tendency value. A signal-to-noise metric to detect a false brady pause may include the post-pause central tendency value and the intra-pause threshold (e.g., a ratio including the pre-pause central tendency value and the intra-pause threshold). The pause detection circuit discards the candidate pause episode or stores the candidate pause episode as a bradycardia pause episode according to the post-pause central tendency value and the intra-pause threshold. For instance, the pause detection may discard the candidate pause episode when a calculated ratio of the post-pause central tendency value to the intra-pause threshold is less than a specified ratio threshold value.

In some examples, the pause detection circuit discards the candidate pause episode or stores the candidate pause episode as a bradycardia pause episode according to the pre-pause central tendency value, the post-pause central tendency value and the intra-pause threshold (e.g., a pre-pause ratio and a post-pause ratio). In some examples, the pause detection circuit rejects the candidate pause episode if a specified number of R-waves are not detected during a specified post-pause duration. For instance, the pause detection circuits may reject the candidate pause episode if four R-waves are not detected within eight seconds after the last R-wave sensed 642 before the detected candidate pause episode.

Other signal-to-noise metrics may be used by the pause detection circuit to determine brady pause or false brady pause. In some examples, the pause detection circuit calculates the pre-pause central tendency value of the R-wave amplitude and calculates the intra-pause threshold for the intra-pause duration using the pre-pause central tendency value (e.g., as a fraction of the pre-pause central tendency value). The pause detection then identifies signal samples during the intra-pause duration that exceed the calculated intra-pause threshold.

When the number of identified signal samples exceeds a specified threshold number of signal samples (e.g., 2% of the number of signal samples included in the intra-pause duration), the pause detection circuit discards the candidate pause episode. This process can be viewed as a shortcut method similar to using a signal-to-noise ratio of the pre-pause central tendency value to the intra-pause threshold. As soon as the number of signal samples exceeds the specified threshold number (e.g., the 2%) it is known that the ratio of the pre-pause central tendency value to the specified amplitude percentile (e.g., the $98^{th}$ percentile) will be less than the specified threshold. The candidate pause episode may be discarded when the number of signal samples exceeds the specified threshold number.

For the flatline method of FIG. 5, candidate pause episodes will be rejected if a significant amount of flatline is evident in the candidate pause signal. There are several potential reasons for flatline data that may manifest as false pauses, including a 'dry' pocket, or loss of electrode contact. These pauses are characterized as extended periods of flat and relatively noiseless signal responses in the decompressed signal.

Figure 7:
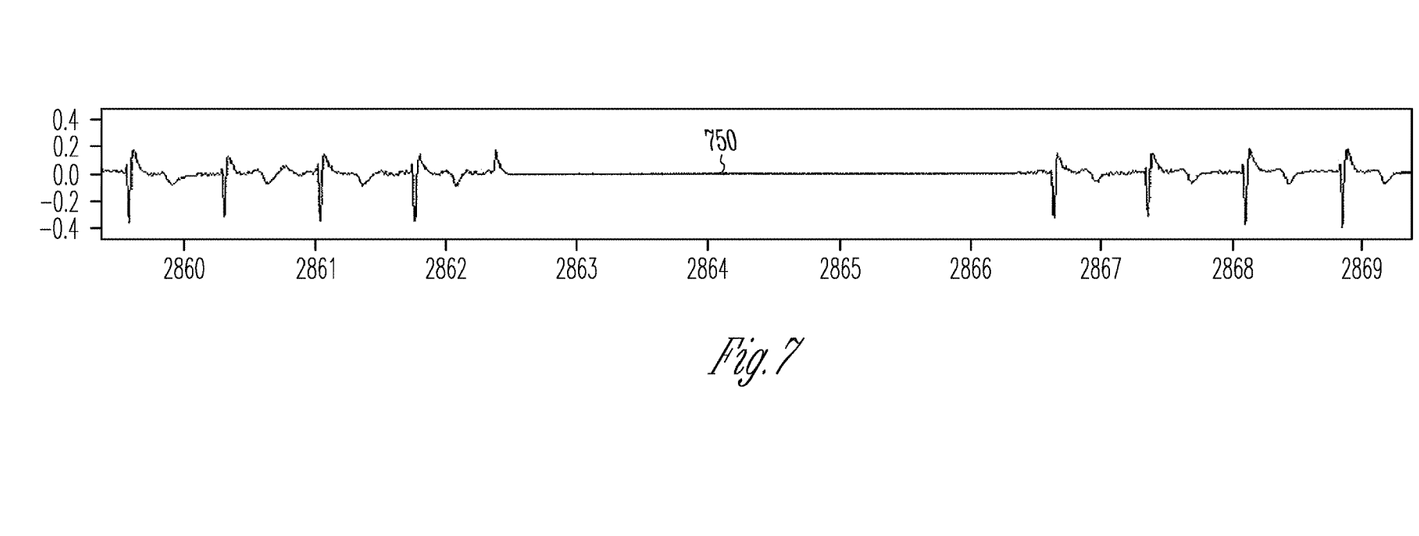
FIG. 7 is an illustration of a signal waveform representing loss of sensing by an ambulatory medical device.

FIG. 7 is an illustration of a flatline episode. True pauses will contain myopotential noise that has significantly higher peak voltages that effectively limit the maximum duration of flat appearing segments in the signal. Episodes with a significant amount of flatline 705 are rejected because flatline represents a loss of appropriate sensing during which time intrinsic cardiac depolarization may have occurred. Signal flatline can be defined as a signal variation that is less than a specified threshold variation. For instance, a run of samples within +/−2 LSB counts can constitute a flatline. Nominally, the threshold variation may be +/−1 LSB counts.

The pause detection circuit may discard the candidate pause episode when detecting that a cardiac signal was not sensed during the candidate pause episode, otherwise the pause detection circuit may store the candidate pause episode as a brady pause episode although the storing is dependent on the other methods of detection being satisfied. In some examples, the pause detection circuit detects that a cardiac signal was not sensed during the candidate pause episode when determining that the magnitude of a specified number of consecutive samples of the sampled cardiac signal is less than a specified threshold sample magnitude. In some examples, the pause detection circuit detects that a cardiac signal was not sensed during the candidate pause episode when determining that the magnitude of samples of the sampled cardiac signal are less than a specified threshold sample magnitude for a specified time duration after detection of the candidate pause episode.

Figure 8:
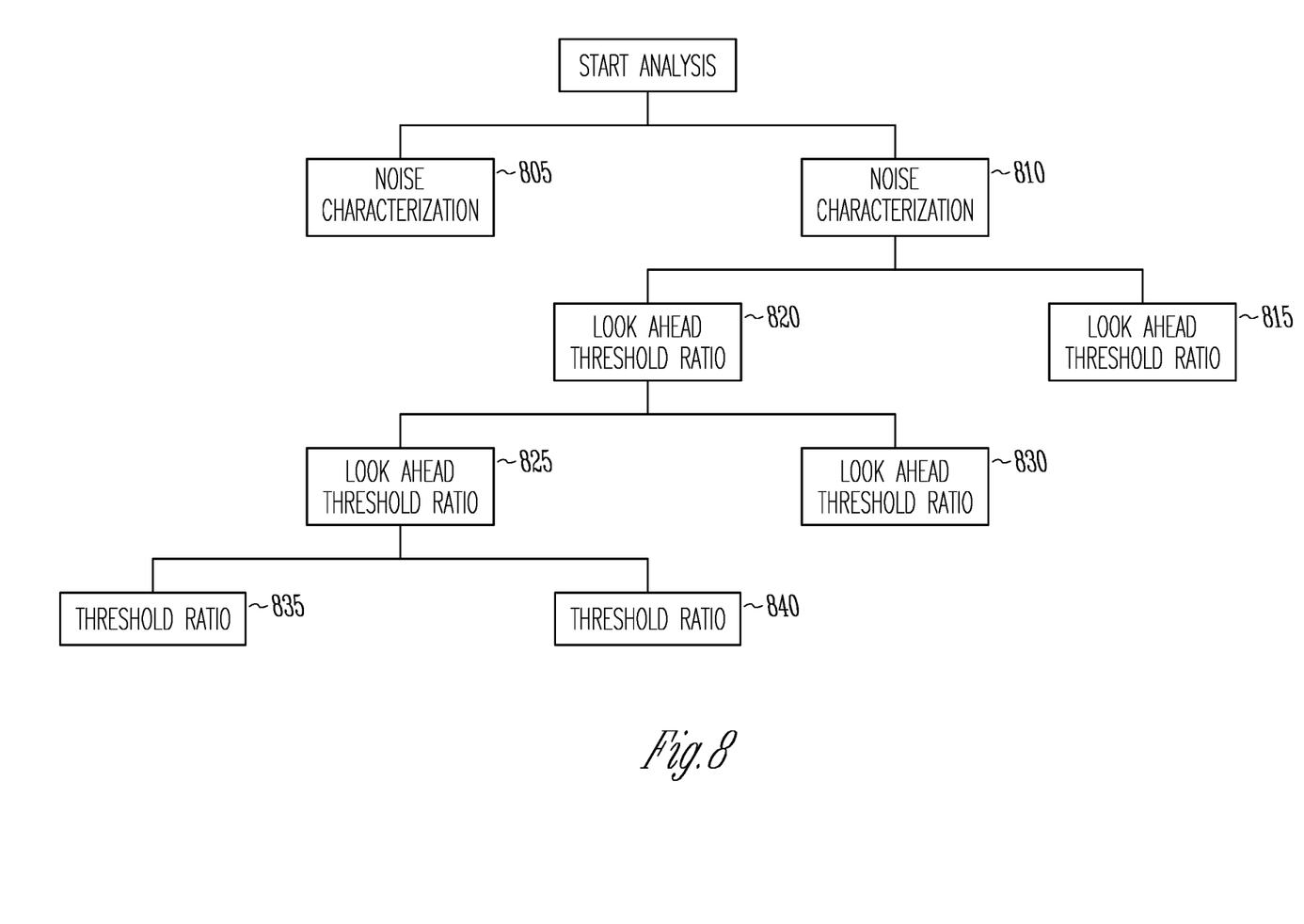
FIG. 8 shows an example of a decision tree for detecting bradycardia pause.

The methods shown in FIG. 5 can be implemented as a decision tree. FIG. 8 shows an example of a decision tree. Each node of the decision tree includes a rule for detecting brady pause. In the example, the first layer of the decision tree includes rules related to noise characterization. If the noise characterization rule for node 805 is satisfied, the candidate pause episode is rejected, if the noise characterization rule for node 810 is satisfied, the brady detection proceeds to the next layer where signal-to-noise metrics are analyzed.

Nodes 815, 820, 825, and 830 include rules for post-pause threshold signal-to-noise ratios. If the rules for nodes 815 or 825 are satisfied, the candidate pause episode is rejected. If the rules for nodes 820 and 830 are satisfied, the brady protection detection proceeds to the next layer of detection at nodes 835, 840 where pre-pause threshold signal-to-noise ratios are analyzed. If the analysis of the candidate pause signal satisfies the rules in the decision tree for true brady pause, the candidate pause episode is stored as a brady pause episode.

The cascade of thresholds used for detection can be used to enhance performance of the detection algorithm. The decision boundary that determines pause versus rejection can be a piecewise linear one in the two-dimensional space created by the pre-pause and post-pause metrics. The decision tree can provide for an efficient implementation of a brady pause detection algorithm. For instance, the least computationally expensive methods can be included in the first layers and can be performed first, which can lead to faster detection and minimize the computation time.

Patient monitoring systems that monitor cardiac function of the patient or subject remote from a clinical setting can lead to improved diagnosis and improved treatment of the patient's condition. The systems and methods described herein can reduce the number of false bradycardia pauses recorded by ambulatory monitoring devices such as ILRs and ICMs. Reducing the recording of false pauses can lead to better use of the time spent by clinicians in analyzing the recorded data.

ADDITIONAL DESCRIPTION AND EXAMPLES

Example 1 includes subject matter comprising: a cardiac signal sensing circuit configured to generate a sensed cardiac signal representative of electrical cardiac activity of a subject; a buffer memory configured to store at least a portion of the cardiac signal; and a pause detection circuit electrically coupled to the cardiac signal sensing circuit and the buffer memory and configured to: identify ventricular depolarization in the cardiac signal or the sampled cardiac signal; detect a candidate pause episode using the cardiac signal in which delay in ventricular depolarization exceeds a specified delay threshold; identify noise events in a stored cardiac signal; and discard the cardiac signal of the candidate pause episode when a number of noise events satisfies a specified noise event number threshold, otherwise store the cardiac signal of the candidate pause episode as a bradycardia pause episode.

In Example 2, the subject matter of Example 1 optionally includes a bandpass filter circuit configured to filter the cardiac signal to a first specified frequency band to produce a first filtered cardiac signal; and a high-pass filter circuit configured to filter the first filtered cardiac signal to a second specified frequency band to produce a second filtered cardiac signal, wherein the pause detection circuit is configured to identify the noise events using the second filtered cardiac signal.

In Example 3, the subject matter of Example 2, optionally includes a low-pass filter circuit configured to filter the first filtered cardiac signal to a third specified frequency band to produce a third filtered cardiac signal, wherein a frequency range of the third frequency band is lower than a frequency range of the second frequency band, and wherein the pause detection circuit is configured to detect ventricular depolarization using the third filtered cardiac signal.

In Example 4, the subject matter of one or any combination of Examples 1-3 optionally includes a pause detection circuit configured to: time a specified intra-pause duration in response to the detecting of the candidate pause episode; determine a post-pause central tendency value of amplitude of a specified number of R-waves identified after the candidate pause episode; calculate an intra-pause threshold of amplitude of signal samples during the intra-pause duration; and discard the candidate pause episode or store the candidate pause episode as a bradycardia pause episode according to the post-pause central tendency value and the intra-pause threshold.

In Example 5, the subject matter of Example 4 optionally includes a pause detection circuit configured to calculate a ratio including the post-pause central tendency value and the intra-pause threshold.

In Example 6, the subject matter of one or both of Examples 4 and 5 optionally includes a pause detection circuit configured to: determine a pre-pause central tendency value of amplitude of a specified number of R-waves identified prior to the candidate pause episode; and discard the candidate pause episode or store the candidate pause episode as a bradycardia pause episode according to the pre-pause central tendency value and the intra-pause threshold.

In Example 7, the subject matter of one or any combination of Examples 1-6 optionally includes a pause detection circuit configured to discard the candidate pause episode when detecting that the cardiac signal was not sensed during the candidate pause episode, otherwise store the candidate pause episode as a bradycardia pause episode.

In Example 8, the subject matter of claim 7 optionally includes a pause detection circuit configured to detect that the cardiac signal was not sensed when determining that magnitude of a specified number of samples of the sampled cardiac signal is less than a specified threshold sample magnitude.

In Example 9, the subject matter of one or any combination of Examples 1-8 optionally includes the cardiac signal sensing circuit, the buffer memory and the pause detection circuit being included in an implantable medical device.

In Example 10, the subject matter of one or any combination of Examples 1-8 optionally includes the cardiac signal sensing circuit and the buffer memory being included in a wearable medical device and the pause detection circuit being included in a separate medical device.

Example 11 can include subject matter (such as an apparatus), or can optionally be combined with one or any combination of Examples 1-10 to include such subject matter, comprising: a cardiac signal sensing circuit configured to generate a sensed cardiac signal and produce a sampled cardiac signal representative of electrical cardiac activity of a subject; a buffer memory configured to store at least a portion of the sampled cardiac signal; and a pause detection circuit electrically coupled to the cardiac signal sensing circuit and the buffer memory and configured to: identify ventricular depolarization R-waves in at least one of the sensed cardiac signal or the sampled cardiac signal; detect a candidate pause episode in which delay between identified R-waves exceeds a specified delay threshold and time a specified intra-pause duration in response to the detecting; calculate an intra-pause threshold of amplitude for signal samples obtained during the intra-pause duration; identify signal samples during the intra-pause duration that exceed the intra-pause threshold; and discard the candidate pause episode or store the candidate pause episode as a bradycardia pause episode according to the identified number of signal samples.

In Example 12, the subject matter of Example 11 optionally includes a pause detection circuit configured to: calculate a pre-pause central tendency value of amplitude of a specified number of R-waves identified prior to the candidate pause episode and calculate the intra-pause threshold using the pre-pause central tendency value; and discard the candidate pause episode when the identified number of signal samples exceeds a specified threshold number of signal samples.

In Example 13, the subject matter of one or both of Examples 11 and 12 optionally includes a pause detection circuit configured to: calculate a pre-pause central tendency value of amplitude of a specified number of R-waves identified prior to the candidate pause episode; calculate the intra-pause threshold according to an amplitude of a specified fraction of the signal samples during the intra-pause duration; and discard the candidate pause episode or store the candidate pause episode as a bradycardia pause episode according to a ratio including the pre-pause central tendency value and the intra-pause threshold.

In Example 14, the subject matter of one or any combination of Examples 11-13 optionally includes a pause detection circuit configured to: calculate a post-pause central tendency value of amplitude of a specified number of R-waves identified prior to the candidate pause episode; calculate the intra-pause threshold according to an amplitude of a specified fraction of the signal samples during the intra-pause duration; and discard the candidate pause episode or store the candidate pause episode as a bradycardia pause episode according to a ratio including the post-pause central tendency value and the intra-pause threshold.

In Example 15, the subject matter of one or any combination of Examples 11-14 optionally includes a pause detection circuit configured to begin timing the intra-pause duration a specified time after a last R-wave sensed before the detected candidate pause episode.

In Example 16, the subject matter of one or any combination of Examples 11-15 optionally includes a pause detection circuit configured to reject the candidate pause episode if a specified number of R-waves are not detected during a specified post-pause duration.

In Example 17, the subject matter of one or any combination of Examples 11-16 optionally includes: a bandpass filter circuit configured to filter the at least one of the sensed cardiac signal or the sampled cardiac signal to remove physiological noise from the signal and generate a first filtered signal; and a high-pass filter circuit configured to filter the first filtered signal to reduce a P-wave signal component in the first filtered signal and generate a second filtered signal, wherein the pause detection circuit is configured to identify ventricular depolarization R-waves using the second filtered signal.

Example 18 can include subject matter (such as an apparatus), or can optionally be combined with one or any combination of Examples 1-17 to include such subject matter, comprising: a cardiac signal sensing circuit configured to generate a sensed cardiac signal and produce a sampled cardiac signal representative of electrical cardiac activity of a subject; a buffer memory configured to store at least a portion of the sampled cardiac signal; and a pause detection circuit electrically coupled to the cardiac signal sensing circuit and the buffer memory and configured to: identify ventricular depolarization in the sampled cardiac signal; detect a candidate pause episode in which delay in ventricular depolarization exceeds a specified delay threshold; and discard the candidate pause episode when detecting that the cardiac signal was not sensed during the candidate pause episode, otherwise store the candidate pause episode as a bradycardia pause episode.

In Example 19, the subject matter of Example 18 can optionally include a pause detection circuit configured to detect that the cardiac signal was not sensed when determining that magnitude of a specified number of consecutive samples of the sampled cardiac signal is less than a specified threshold sample magnitude.

In Example 20, the subject matter of one or both of Examples 18 and 19 can optionally include a pause detection circuit configured to detect that the cardiac signal was not sensed when determining that magnitude of samples of the sampled cardiac signal is less than a specified threshold sample magnitude for a specified time duration after detection of the candidate pause episode.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These several non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a cardiac signal sensing circuit configured to receive a cardiac signal representative of electrical cardiac activity of a subject;
   a buffer memory configured to store at least a portion of the cardiac signal; and
   a pause detection circuit electrically coupled to the cardiac signal sensing circuit and the buffer memory and configured to:
      identify ventricular depolarization in the cardiac signal or the sampled cardiac signal;
      detect a candidate pause episode using the cardiac signal in which delay in ventricular depolarization exceeds a specified delay threshold;
      identify noise events in a stored cardiac signal; and
      discard the cardiac signal of the candidate pause episode when a number of noise events satisfies a specified noise event number threshold, otherwise store the cardiac signal of the candidate pause episode as a bradycardia pause episode.

2. The apparatus of claim 1, including: a bandpass filter circuit configured to filter the cardiac signal to a first specified frequency band to produce a first filtered cardiac signal; and a high-pass filter circuit configured to filter the first filtered cardiac signal to a second specified frequency band to produce a second filtered cardiac signal, wherein the pause detection circuit is configured to identify the noise events using the second filtered cardiac signal.

3. The apparatus of claim 2, including a low-pass filter circuit configured to filter the first filtered cardiac signal to a third specified frequency band to produce a third filtered cardiac signal, wherein a frequency range of the third frequency band is lower than a frequency range of the second frequency band, and wherein the pause detection circuit is configured to detect ventricular depolarization using the third filtered cardiac signal.

4. The apparatus of claim 1, wherein the pause detection circuit is configured to:
   time a specified intra-pause duration in response to the detecting of the candidate pause episode;
   determine a post-pause central tendency value of amplitude of a specified number of R-waves identified after the candidate pause episode;
   calculate an intra-pause threshold of amplitude of signal samples during the intra-pause duration; and
   discard the candidate pause episode or store the candidate pause episode as a bradycardia pause episode according to the post-pause central tendency value and the intra-pause threshold.

5. The apparatus of claim 4, wherein the pause detection circuit is configured to calculate a ratio including the post-pause central tendency value and the intra-pause threshold.

6. The apparatus of claim 4, wherein the pause detection circuit is configured to:
   determine a pre-pause central tendency value of amplitude of a specified number of R-waves identified prior to the candidate pause episode; and
   discard the candidate pause episode or store the candidate pause episode as a bradycardia pause episode according to the pre-pause central tendency value and the intra-pause threshold.

7. The apparatus of claim 1, wherein the pause detection circuit is configured to discard the candidate pause episode when detecting that the cardiac signal was not sensed during the candidate pause episode, otherwise store the candidate pause episode as a bradycardia pause episode.

8. The apparatus of claim 7, wherein the pause detection circuit is configured to detect that the cardiac signal was not sensed when determining that magnitude of a specified number of samples of the sampled cardiac signal is less than a specified threshold sample magnitude.

9. The apparatus of claim 1, wherein the cardiac signal sensing circuit, the buffer memory and the pause detection circuit are included in an implantable medical device.

10. The apparatus of claim 1, wherein the cardiac signal sensing circuit and the buffer memory are included in a wearable medical device and the pause detection circuit is included in a separate medical device.

11. An apparatus comprising:
   a cardiac signal sensing circuit configured to receive a sensed cardiac signal and produce a sampled cardiac signal representative of electrical cardiac activity of a subject;

a buffer memory configured to store at least a portion of the sampled cardiac signal; and a pause detection circuit electrically coupled to the cardiac signal sensing circuit and the buffer memory and configured to:

identify ventricular depolarization R-waves in at least one of the sensed cardiac signal or the sampled cardiac signal;

detect a candidate pause episode in which delay between identified R-waves exceeds a specified delay threshold and time a specified intra-pause duration in response to the detecting;

calculate an intra-pause threshold of amplitude for signal samples obtained during the intra-pause duration;

identify signal samples during the intra-pause duration that exceed the intra-pause threshold; and discard the candidate pause episode or store the candidate pause episode as a bradycardia pause episode according to the identified number of signal samples.

12. The apparatus of claim 11, wherein the pause detection circuit is configured to:

calculate a pre-pause central tendency value of amplitude of a specified number of R-waves identified prior to the candidate pause episode and calculate the intra-pause threshold using the pre-pause central tendency value; and discard the candidate pause episode when the identified number of signal samples exceeds a specified threshold number of signal samples.

13. The apparatus of claim 11, wherein the pause detection circuit is configured to:

calculate a pre-pause central tendency value of amplitude of a specified number of R-waves identified prior to the candidate pause episode;

calculate the intra-pause threshold according to an amplitude of a specified fraction of the signal samples during the intra-pause duration; and discard the candidate pause episode or store the candidate pause episode as a bradycardia pause episode according to a ratio including the pre-pause central tendency value and the intra-pause threshold.

14. The apparatus of claim 11, wherein the pause detection circuit is configured to:

calculate a post-pause central tendency value of amplitude of a specified number of R-waves identified prior to the candidate pause episode;

calculate the intra-pause threshold according to an amplitude of a specified fraction of the signal samples during the intra-pause duration; and discard the candidate pause episode or store the candidate pause episode as a bradycardia pause episode according to a ratio including the post-pause central tendency value and the intra-pause threshold.

15. The apparatus of claim 11, wherein the pause detection circuit is configured to begin timing the intra-pause duration a specified time after a last R-wave sensed before the detected candidate pause episode.

16. The apparatus of claim 11, wherein the pause detection circuit is configured to reject the candidate pause episode if a specified number of R-waves are not detected during a specified post-pause duration.

17. The apparatus of claim 11, including:

a bandpass filter circuit configured to filter the at least one of the sensed cardiac signal or the sampled cardiac signal to remove physiological noise from the signal and generate a first filtered signal; and a high-pass filter circuit configured to filter the first filtered signal to reduce a P-wave signal component in the first filtered signal and generate a second filtered signal, wherein the pause detection circuit is configured to identify ventricular depolarization R-waves using the second filtered signal.

18. An apparatus comprising:

a cardiac signal sensing circuit configured to receive a sensed cardiac signal and produce a sampled cardiac signal representative of electrical cardiac activity of a subject;

a buffer memory configured to store at least a portion of the sampled cardiac signal; and a pause detection circuit electrically coupled to the cardiac signal sensing circuit and the buffer memory and configured to:

identify ventricular depolarization in the sampled cardiac signal;

detect a candidate pause episode in which delay in ventricular depolarization exceeds a specified delay threshold; and discard the candidate pause episode when detecting that the cardiac signal was not sensed during the candidate pause episode, otherwise store the candidate pause episode as a bradycardia pause episode.

19. The apparatus of claim 18, wherein the pause detection circuit is configured to detect that the cardiac signal was not sensed when determining that magnitude of a specified number of consecutive samples of the sampled cardiac signal is less than a specified threshold sample magnitude.

20. The apparatus of claim 18, wherein the pause detection circuit is configured to detect that the cardiac signal was not sensed when determining that magnitude of samples of the sampled cardiac signal is less than a specified threshold sample magnitude for a specified time duration after detection of the candidate pause episode.

* * * * *